United States Patent
Penny

(10) Patent No.: US 11,135,024 B2
(45) Date of Patent: Oct. 5, 2021

(54) SYSTEM AND METHOD FOR VERIFYING END EFFECTOR/INSTRUMENT ENGAGEMENT TO A ROBOTIC MANIPULATOR

(71) Applicant: Asensus Surgical US, Inc., Durham, NC (US)

(72) Inventor: Matthew R Penny, Holly Springs, NC (US)

(73) Assignee: Asensus Surgical US, Inc., Durham, NC (US)

( * ) Notice: Subject to any disclaimer, the term of this patent is extended or adjusted under 35 U.S.C. 154(b) by 0 days.

(21) Appl. No.: 15/975,760

(22) Filed: May 9, 2018

(65) Prior Publication Data

US 2020/0375672 A1    Dec. 3, 2020

Related U.S. Application Data

(60) Provisional application No. 62/503,359, filed on May 9, 2017.

(51) Int. Cl.
| | | |
|---|---|---|
| *A61B 34/30* | (2016.01) | |
| *A61B 34/00* | (2016.01) | |
| *A61B 17/00* | (2006.01) | |
| *A61B 90/50* | (2016.01) | |
| *A61B 90/00* | (2016.01) | |
| *A61B 34/20* | (2016.01) | |

(52) U.S. Cl.
CPC .............. *A61B 34/30* (2016.02); *A61B 34/76* (2016.02); *A61B 34/77* (2016.02); *A61B 90/50* (2016.02); *A61B 2017/00119* (2013.01); *A61B 2034/2048* (2016.02); *A61B 2090/066* (2016.02); *A61B 2090/0808* (2016.02)

(58) Field of Classification Search
CPC ......... A61B 34/30; A61B 34/76; A61B 34/77; A61B 90/50; A61B 2017/00119
See application file for complete search history.

(56) References Cited

U.S. PATENT DOCUMENTS

2017/0261348 A1\* 9/2017 LeBoeuf, II ........... A61B 34/70

\* cited by examiner

*Primary Examiner* — Paula J Stice

(57) ABSTRACT

A robotic surgical system is configured to determine whether a surgical instrument has been properly mounted to an arm of the surgical system. As the surgical instrument is moved into engagement with the arm, a magnet on the arm exerts an attractive force on a plate on the surgical instrument. As the instrument engages to the arm, load cell measurements and inertial measurement unit (IMU) information from one or more sensors on the arm are monitored to determine the mass of the instrument as well as the acceleration of the instrument as it mates with the instrument engagement interface. The system compares the load cell measurements and IMU information with what those parameters are expected to be when a surgical device assembly or instrument of that type is mounted. If the load cell measurements and IMU information deviates from what is expected, the system provides a notification to the user and prevents use of the manipulator arm until the surgical device assembly or instrument is properly positioned.

14 Claims, 3 Drawing Sheets

SYSTEM AND METHOD FOR VERIFYING END EFFECTOR/INSTRUMENT ENGAGEMENT TO A ROBOTIC MANIPULATOR

This application claims the benefit of U.S. Provisional Application No. 62/503,359, filed May 9, 2017.

BACKGROUND

There are various types of surgical robotic systems on the market or under development. Some surgical robotic systems use a plurality of robotic arms. Each arm carries a surgical instrument, or the camera used to capture images from within the body for display on a monitor. See U.S. Pat No. 9,358,682 and U.S. 20160058513. Other surgical robotic systems use a single arm that carries a plurality of instruments and a camera that extend into the body via a single incision. See WO 2016/057989. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

It is common that robotic surgical systems include surgical device assemblies that are removably mounted to the manipulator arms. This allows the users to remove and replace the instrument mounted to any given manipulator during the course of a surgical procedure. The engagement of instruments to the robotic manipulator is critical to proper functioning of the system. Improper engagement can result in backlash in the system that could manifest itself in use errors such as imprecise or improper motion and/or function of the surgical instrument.

This application describes the use of force and/or acceleration information provided by force/torque sensors of a robotic system to determine whether an instrument or surgical device assembly effector has been successfully engaged to the robotic manipulator arm.

DETAILED DESCRIPTION

Figure 1:
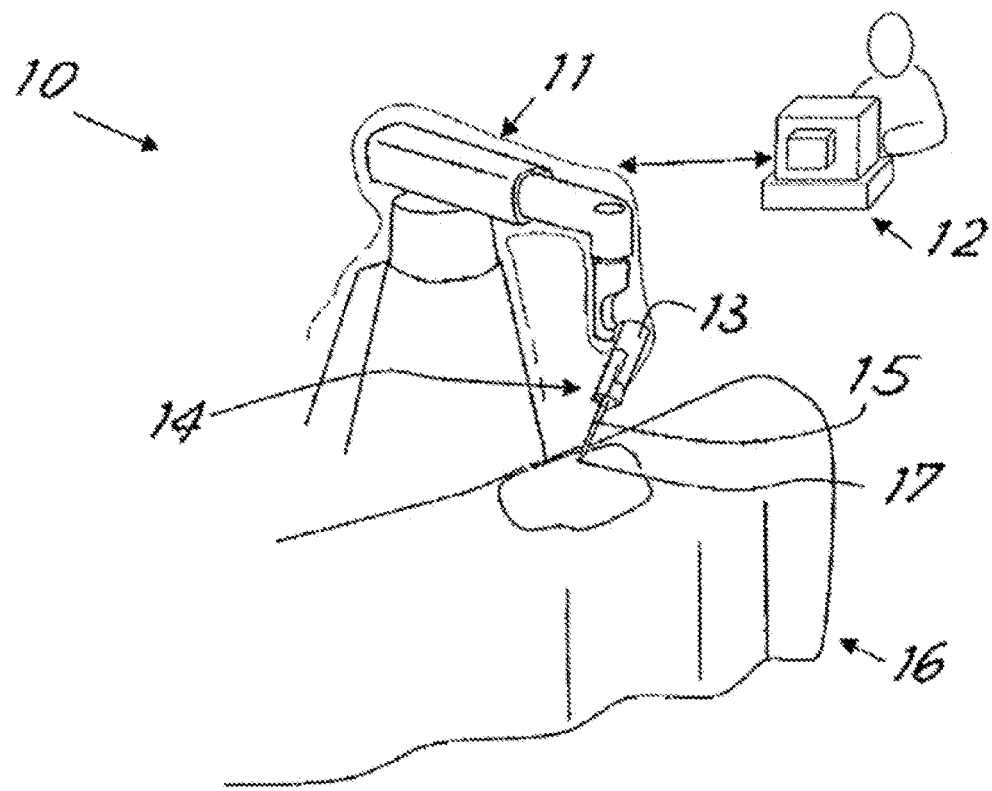
FIG. 1 schematically illustrates a robotic manipulator of a type used in robotic surgical procedures.

FIG. 1 shows components of a robotic surgical system 10 of the type described in U.S. Pat. No. 9,358,682 and U.S. 20160058513. Features of the system 10 are shown to facilitate an understanding of the way in which the concepts of the present invention may be implemented, but it should be understood that the invention may be used with a variety of different surgical or industrial robotic systems and is not limited to use with system 10.

System 10 comprises at least one robotic manipulator arm 11 which operates under the control of a command console (not shown) operated by the surgeon, as described in the Background. The robotic manipulator (or each robotic manipulator) has a terminal portion 13 designed to support, position and orient a surgical device assembly 14. The surgical device assembly includes a surgical instrument having shaft 15 and a distal end effector 17 positionable within a patient 16.

The surgical device assembly includes a proximal part that is received by the terminal portion 13 of the robotic manipulator. In the illustrated configuration, the surgical device assembly includes a proximal housing 20 that is received by the terminal portion 13 at an instrument engagement interface as shown.

Figure 2:
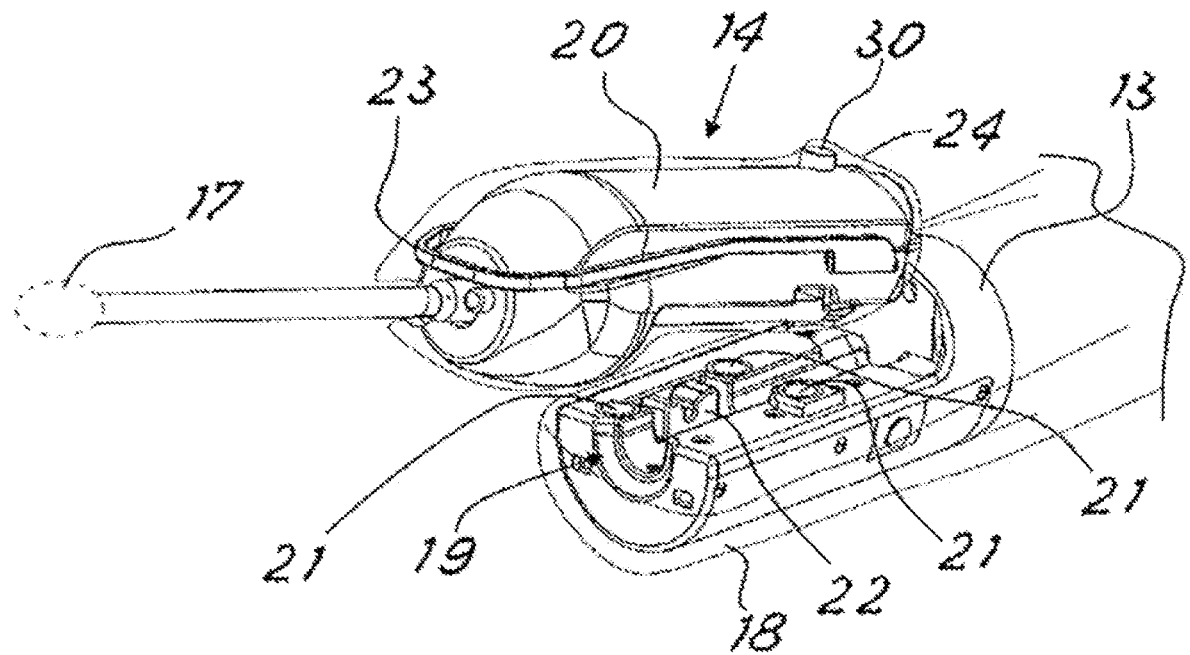
FIG. 2 illustrates the step of mounting of a surgical device onto the manipulator of FIG. 1.

The end effector 17 may be one of many different types of that are used in surgery including, without limitation, end effectors 17 having one or more of the following features: jaws that open and close, joints that articulate in one or more degrees of freedom at one or more discrete joints, distal shaft sections that bend, a tip that rolls axially relative to the shaft 15, a tip mounted on a shaft that rolls axially relative to the manipulator arm 11. For the sake of simplicity, in FIG. 2 the end effector 17 is shown as an oval form in broken lines.

The system includes instrument actuators for driving the motion of the end effector 17. These actuators, which might be motors or other types of actuators (e.g. hydraulic/pneumatic), are positioned in the terminal portion 13 of the robotic manipulator, or in the housing 20 of the surgical device assembly, or some combination of the two. In the latter example, some motion of the end effector might be driven using one or more motors/actuators in the terminal portion 13 of the robotic manipulator, while other motion might be driven using motors/actuators in the housing 20. Where actuators in the terminal portion 13 are used to drive jaw open/close or other motion of a portion of the end effector or instrument, the housing includes mechanical transmission features that operably couple with one or more drive outputs at the terminal portion so that motion from the drive output is transferred to the surgical instrument. As one non-limiting example of this concept, in the embodiment shown in FIG. 2, terminal portion includes a sled 22 that is longitudinally moveable along the terminal portion 13. A pin (not shown) extends laterally from the housing 20 and is received in the sled 22. The sled 22 is driven by a motor in the surgical manipulator to transmit motion to the pin, causing the pin to move relative to the housing 20. The pin is coupled to actuation elements (e.g. push and/or pull rods) in the instrument that drive open/close of the end effector jaws. When the robotic system receives a command from the surgeon console instructing the system to open or close the jaws, the motor drives the sled 22 to advance or retract the pin, thus opening or closing the jaws.

During use, the robotic system controls movement of the robotic manipulator and movement of the end effector (e.g. jaw open/close, tip roll, articulating or bending, etc.) based on surgeon input received by the system via the console 12. The control signals used to generate the various types of movement depend in some cases on the geometry, length, weight, jaw open-close ranges, or other parameters of the surgical instrument 14. The system may receive input concerning the relevant parameters in a number of different ways. As one example, the system can read from a memory device, bar code, RFID tag etc on the instrument the parameters themselves or information identifying the instrument or type of instrument so that the system can use that information to obtain the relevant parameters from system memory. As another example, the user input device can be used to input to the system information specifying the relevant parameters or information identifying the instrument allowing the system to look up the parameters from system memory. Other mechanisms allowing the system to "know" the relevant parameters of the instrument may be used without departing from the scope of this disclosure.

U.S. Patent Publication U.S. 2010/0094312 (the '312 application), describes a surgical robotic system in which sensors are used to determine the forces that are being applied to the patient by the robotic surgical tools during use. The application describes the use of a 6 DOF force/torque sensor attached to a surgical robotic manipulator as a method for determining the haptic information needed to provide force feedback to the surgeon at the user interface. It describes a method of force estimation and a minimally invasive medical system, in particular a laparoscopic system, adapted to perform this method. As described in the '312, a robotic manipulator has an effector unit equipped with a six degrees-of-freedom (6-DOF or 6-axes) force/torque sensor. The effector unit is configured for holding a minimally invasive instrument mounted thereto. In normal use, a first end of the instrument is mounted to the effector unit of the robotic arm and the opposite, second end of the instrument (e.g. the instrument tip) is located beyond an external fulcrum (pivot point kinematic constraint) that limits the instrument in motion. In general, the fulcrum is located within an access port (e.g. the trocar) installed at an incision in the body of a patient, e.g. in the abdominal wall. A position of the instrument relative to the fulcrum is determined using the 6 DOF force/torque sensor. During surgery, using the 6 DOF force/torque sensor, a force and a torque exerted onto the effector unit by the first end of the instrument are measured, and an estimate of a force exerted onto the second end of the instrument based on the determined position is calculated. The forces are communicated to the surgeon in the form of tactile haptic feedback at the hand controllers of the surgeon console. This force sensor enables the system to measure the forces applied at any location distal to the sensor.

In other robotic systems, the joints within the robotic arm may include force/torque sensors that help determine forces at a specific joint, as well as those forces applied distal to each sensor. A robotic arm such as the LWR manufactured by Kuka Robotics, for example, is equipped with force/torque sensors at each of its 7 joints. Output from these sensors, when combined with the kinematic relationship of the joints, can be used to determine the forces applied at the robotic end effector.

The present invention provides a system and method for confirming that a surgical instrument is properly positioned on a robotic manipulator. The system and method may be used to determine proper positioning of a surgical device assembly that may include electromechanical or fluid actuators in a housing 20 as described, or that might be a surgical instrument having a housing 20 without such actuators, or that might be a surgical camera or laparoscope. For simplicity, the term "surgical instrument" may be used below to refer to any of these or any other type of suitable configuration.

In general, novel aspects of the present invention include the use of the force and/or acceleration measurements of a robotic manipulator system to identify whether or not an instrument has been engaged properly. These measurements may reflect both mass gains as well as momentum of an object that is attracted to, or repelled from, the robotic system via magnetic forces such as those from magnets used to help engage the surgical instrument to the robotic manipulator. The measurements also reflect the acceleration of the instrument during engagement, which can be monitored to identify the success of engagement.

Figure 3A:
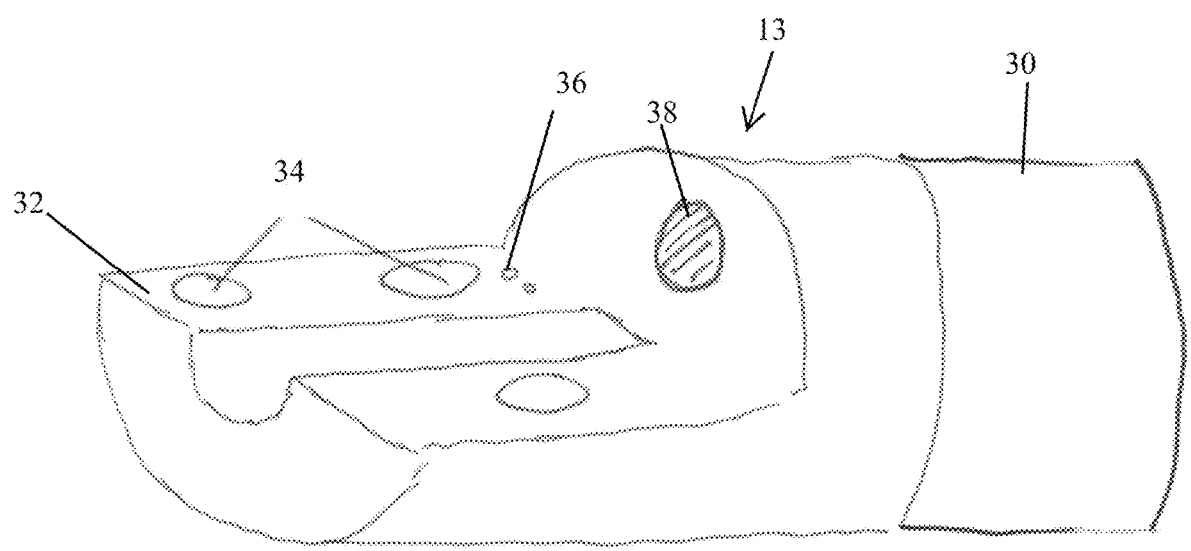
FIG. 3A shows a distal portion of the manipulator of FIG. 1.
Figure 3B:
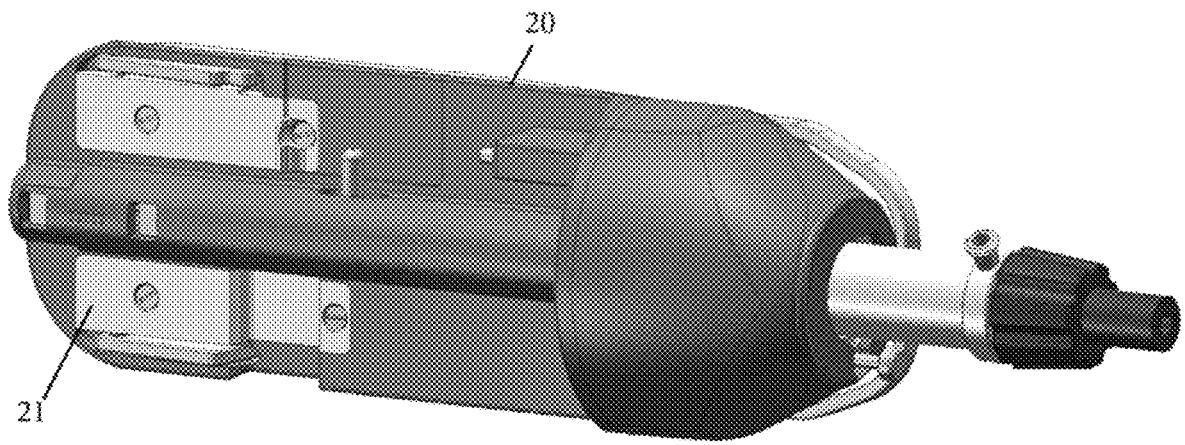
FIG. 3B shows the underside of the proximal housing engageable with the distal portion of the manipulator shown in FIG. 3A.

Referring to FIG. 3, in one embodiment the robotic manipulator 11 has an instrument engagement interface 32 configured to receive a surgical instrument. For the purposes of this discussion, the system will be described with reference to a surgical instrument that includes the proximal housing 20, but it is to be understood that this is not intended to limit the scope of the invention to this particular configuration.

The robotic manipulator 11 incorporates a six degree of freedom force sensor 30 with an internal inertial measurement unit (IMU). This force sensor is positioned distal to all of the joints of the manipulator arm, but proximal to the instrument engagement interface 32. This may be a configuration similar to that described in U.S. Patent Publication U.S. 2010/0094312.

The instrument engagement interface 32 incorporates one or more magnets 34 that attract a steel plate on the underside of the portion of the surgical instrument, in this case housing 20, that engages with the interface 32. An instrument presence sensor, which may be an inductive sensor 36 that detects the presence of a metal component of the surgical instrument or housing 20 or one or more optical sensors that are blocked when the surgical device is positioned on the interface, is positioned at the terminal portion 13 to register that the surgical instrument has been mounted at the interface 32.

Just prior to engagement of the surgical device assembly housing 20 or surgical instrument to the engagement interface, the attractive force of the magnet is exerted on the steel plate. As the instrument engages to the robotic arm, the load cell measurements and IMU information from the sensor 30 are monitored to determine both the mass of the instrument as well as the acceleration of the instrument as it mates with the instrument engagement interface. For each instrument/surgical device assembly type to be mounted to the manipulator arm, the system is programmed to compare the load cell measurements and IMU information with what those parameters are expected to be when a surgical device assembly or instrument of that type is mounted. If the load cell measurements and IMU information deviates from what is expected, the system provides a notification to the user (e.g. a visible, audible, and/or vibratory alert) and/or prevents use of the manipulator arm under the surgical device assembly or instrument is properly positioned.

The features described above that allow the system to receive or determine input concerning the relevant geometry or other parameters of the surgical instrument may also be used to allow the system to receive or determine the expected load cell measurements and IMU information useful to confirm proper placement of the surgical instrument. For example, an RFID detector or reader 38 may be positioned to read instrument information from an RFID tag in some portion of the instrument.

The force profile may be used in conjunction with other components that are used to register the presence of an instrument or surgical device assembly on the manipulator arm. For example, input from the instrument presence sensor may be used to initiate the review of data obtained from the sensor 30 and to confirm whether there is proper instrument engagement with the system.

Figure 4:
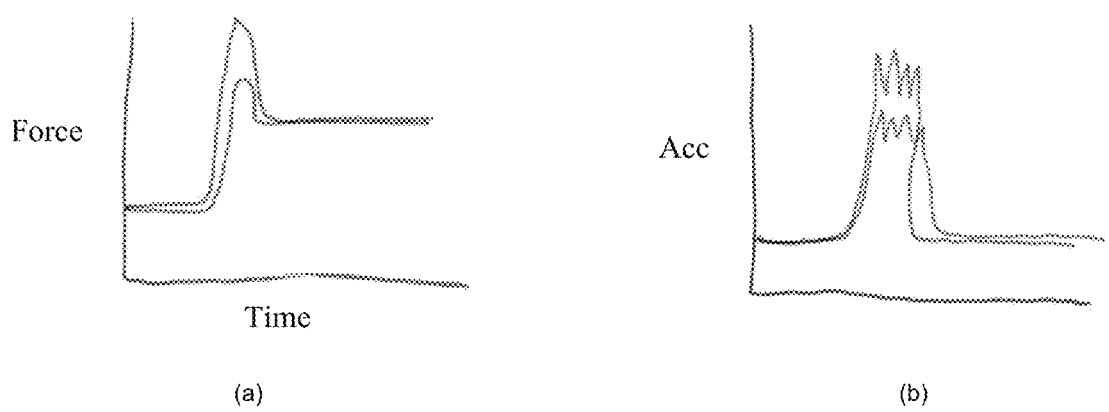
FIGS. 4(a) and (b) shows exemplary force and acceleration profiles of a secure instrument engagement and a misaligned improper instrument engagement.

Referring to FIGS. 4(a) and (b), the force measured by the sensor 30 should indicate the additional mass of the instrument or surgical device assembly after it is engaged with the robotic system. However, at the instant of engagement, the force should spike, before settling at the new value. The amplitude and bandwidth of this spike may be monitored to estimate whether the instrument is properly engaged with the system. Additionally, the acceleration of the IMU can also be monitored. The acceleration profile should start with some value before engagement and should return to a similar value after engagement. Again, the amplitude and bandwidth of the spike during engagement can be monitored to determine the success of the engagement.

Figure 5:
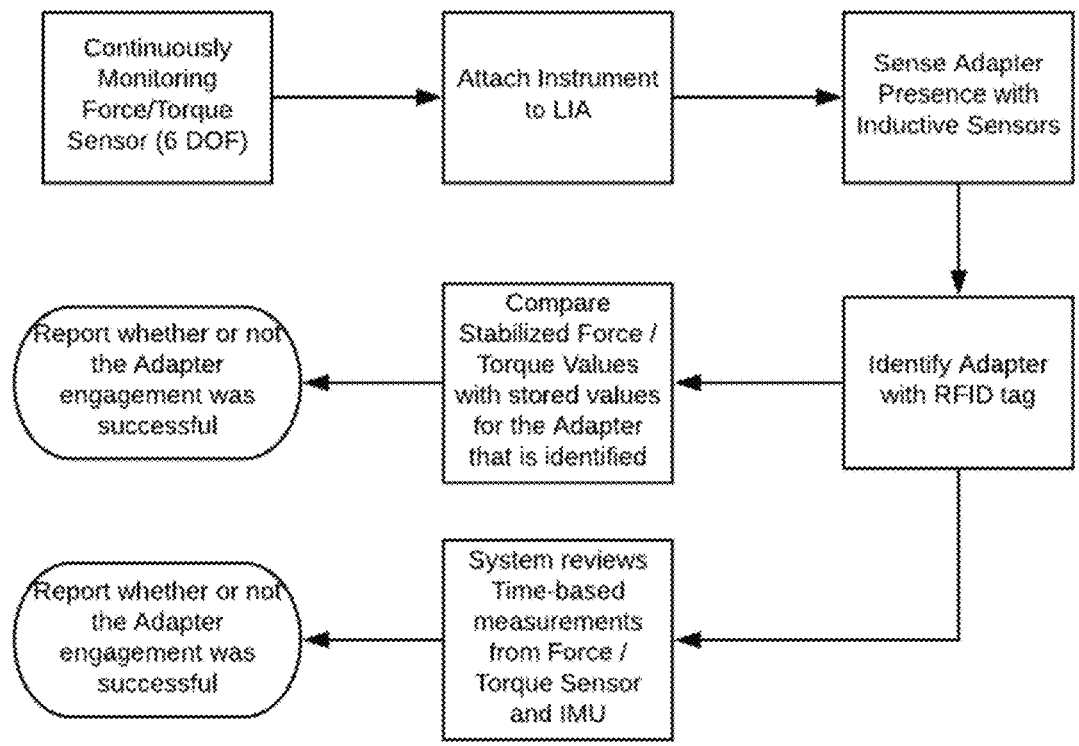
FIG. 5 is a flow diagram illustrating the disclosed method.

The method using the disclosed system is illustrated in FIG. 5. As force/torque is continuously monitored, an instrument is mounted to the terminal portion of the robotic arm (LIA). The presence of the proximal housing ("adapter") on the terminal portion is sensed using the inductive sensors, and the instrument is identified by the system as described above. After a period of time following placement of the instrument, the force/torque values are compared with stored values for the instrument that is identified. The user is alerted as to whether engagement was successful or unsuccessful, the latter being the conclusion if the determined force/torque deviates substantially from the stored values. The system further reviews time-based measurements from the force/torque sensor and the IMU, and the user is alerted as to whether engagement was successful. In one embodiment, the user will be alerted of an unsuccessful engagement if either the force or acceleration profile indicates an error.

A second embodiment utilizes force/torque sensors positioned at each joint in a robotic manipulator. When combining the force/torque sensor information with the kinematic relationships of the robotic manipulator system, the force at the end effector can be determined with some degree of accuracy. As with the first embodiment, the force measurements may be monitored during instrument engagement, enabling a distinction to be made between proper engagement and a false positive engagement of the instrument to the system.

All patents and patent applications referred to herein, including for purposes of priority, are incorporated herein by reference.

What is claimed is:

1. A method for determining proper engagement of an instrument to a robotic manipulator of a robotic surgical system, comprising:
    positioning a surgical instrument on a robotic manipulator;
    measuring force against the robotic manipulator;
    determining a change in force against the robotic manipulator in response to the positioning of the instrument;
    comparing the measured change in force with a change in force expected to result from mounting of the surgical instrument to the robotic manipulator; and
    if the measured change in force and the expected change in force differ by more than a predetermined amount, providing feedback alerting the user.

2. The method of claim 1, further including the step of, if the measured change in force and the expected change in force differ by more than a predetermined amount, preventing operation of at least one of the robotic manipulator and the surgical instrument until the instrument is determined to be properly engaged with the robotic manipulator.

3. The method of claim 1, wherein the force is measured using output from a 6 DOF force/torque sensor of the robotic manipulator.

4. The method of claim 3, wherein the method further includes:
    after positioning the surgical instrument on the robotic manipulator, causing the robotic manipulator to move the surgical instrument in a body cavity in response to user input; and
    during movement of the surgical instrument in the body cavity, measuring forces on the instrument using output from the 6 DOF force/torque sensor of the robotic manipulator.

5. The method of claim 1, wherein the change in force is determined using output from a plurality of force/torque sensors positioned at a plurality of joints of the robotic manipulator.

6. The method of claim 5 wherein the method further includes:
    after positioning the surgical instrument on the robotic manipulator, causing the robotic manipulator to move the surgical instrument in a body cavity in response to user input; and
    during movement of the surgical instrument in the body cavity, measuring forces on the instrument using output from said plurality of force/torque sensors positioned at said plurality of joints of the robotic manipulator.

7. The method of claim 1, wherein the comparing step includes:
    receiving or generating input corresponding to the type of surgical instrument mounted to the robotic manipulator;
    using the input, retrieving or determining the change in force expected to result from mounting of the surgical instrument to the robotic manipulator.

8. The method of claim 1, wherein the method further includes detecting the presence of the surgical instrument using an instrument presence sensor on the robotic manipulator and, in response to detecting the presence of the surgical instrument, determining the change in force.

9. The method of claim 8, wherein the instrument presence sensor is an inductive sensor.

10. The method of claim 8, wherein the instrument presence sensor is an optical sensor.

11. A method for determining proper engagement of an instrument to a robotic manipulator, comprising:
    positioning a surgical instrument on a robotic manipulator;
    using an inertial measurement unit on the robotic manipulator, monitoring acceleration at the distal part of the robotic manipulator over a period of time in response to the positioning of the instrument;
    comparing the acceleration over the period of time with an acceleration expected to result from mounting of the surgical instrument to the robotic manipulator.

12. The method of claim 11, wherein the comparing step includes:
    receiving or generating input corresponding to the type of surgical instrument mounted to the robotic manipulator;
    using the input, retrieving or determining the acceleration over the period of time expected to result from mounting of the surgical instrument to the robotic manipulator.

13. The method of claim 11, further including the step of, if the acceleration over the period of time and the expected acceleration over the period of time differ by more than a predetermined amount, providing feedback alerting the user.

14. The method of claim 11, further including the step of, if the acceleration over the period of time and the expected acceleration over the period of time differ by more than a predetermined amount, preventing operation of at least one of the robotic manipulator and the surgical instrument until the instrument is determined to be properly engaged with the robotic manipulator.

\* \* \* \* \*